United States Patent
Keener et al.

(10) Patent No.: US 9,539,352 B2
(45) Date of Patent: *Jan. 10, 2017

(54) METHOD AND SYSTEM FOR TREATING PACKAGED PRODUCTS

(71) Applicant: Purdue Research Foundation, West Lafayette, IN (US)

(72) Inventors: Kevin M. Keener, Attica, IN (US); Paul A. Klockow, South Bend, IN (US)

(73) Assignee: Purdue Research Foundation, West Lafayette, IN (US)

( * ) Notice: Subject to any disclaimer, the term of this patent is extended or adjusted under 35 U.S.C. 154(b) by 330 days.

This patent is subject to a terminal disclaimer.

(21) Appl. No.: 13/793,342

(22) Filed: Mar. 11, 2013

(65) Prior Publication Data
US 2013/0189156 A1    Jul. 25, 2013

Related U.S. Application Data

(60) Division of application No. 12/861,106, filed on Aug. 23, 2010, now Pat. No. 9,363,880, which is a
(Continued)

(51) Int. Cl.
*B01J 19/08*  (2006.01)
*A61L 2/20*   (2006.01)
(Continued)

(52) U.S. Cl.
CPC . *A61L 2/20* (2013.01); *A23B 7/01* (2013.01); *A23B 7/015* (2013.01); *A23L 3/01* (2013.01);
(Continued)

(58) Field of Classification Search
CPC .......... H05H 1/2406; A23L 3/263; A61L 2/14
(Continued)

(56) References Cited

U.S. PATENT DOCUMENTS 5,316,739 A * 5/1994 Yoshikawa et al. ...... 422/186.05
6,007,770 A * 12/1999 Peiper et al. ........... 422/22
(Continued)

OTHER PUBLICATIONS

US Office Action in related U.S. Appl. No. 12/861,106 mailing date (Aug. 20, 2015 (16 pgs).
(Continued)

*Primary Examiner* — Kevin Joyner
(74) *Attorney, Agent, or Firm* — Brinks Gilson & Lione

(57) ABSTRACT

A system and method for decontamination of product is described. An object to be treated, which may be a food product or a medical device, is placed in a substantially closed dielectric container with a working gas. The container is placed in an apparatus capable of producing a controlled electrical discharge so as to create reactive ion species within the package. The object to be treated may be exposed either the immediate products of the electrical discharge or the long lasting reactive ion species, or both, so as to treat the object to reduce or eliminate specific contaminants, which may be biological pathogens or the cause of product spoilage, or inorganic contaminants. The reactive ion species may result from an atmospheric non-equilibrium plasma (ANEP) formed by the apparatus and the treatment may be performed without significantly increasing the bulk temperature of the object being treated.

57 Claims, 5 Drawing Sheets

Related U.S. Application Data continuation-in-part of application No. 12/726,097, filed on Mar. 17, 2010, now abandoned.

(60) Provisional application No. 61/162,785, filed on Mar. 24, 2009, provisional application No. 61/306,774, filed on Feb. 22, 2010.

(51) Int. Cl.

| | |
|---|---|
| *A23L 3/26* | (2006.01) |
| *A61L 2/22* | (2006.01) |
| *H05H 1/24* | (2006.01) |
| *A23L 3/01* | (2006.01) |
| *A23L 3/32* | (2006.01) |
| *A23B 7/01* | (2006.01) |
| *A23B 7/015* | (2006.01) |

(52) U.S. Cl.
CPC .................. *A23L 3/263* (2013.01); *A23L 3/32* (2013.01); *A61L 2/22* (2013.01); *H05H 1/2406* (2013.01); *H05H 2001/2412* (2013.01); *H05H 2245/1225* (2013.01)

(58) Field of Classification Search
USPC ....................................... 422/186.04, 186.05
See application file for complete search history.

(56) References Cited

U.S. PATENT DOCUMENTS

2009/0010818 A1\* 1/2009 Song ........................ 422/186.05
2010/0032285 A1\* 2/2010 Thomas et al. ............... 204/164

OTHER PUBLICATIONS

Response to U.S. Non-Final Office Action mailing date Aug. 20, 2015 mailed to USPTO on Oct. 20, 2015 (12 pgs).

\* cited by examiner

METHOD AND SYSTEM FOR TREATING PACKAGED PRODUCTS

RELATED APPLICATIONS

This application is divisional application of U.S. Ser. No. 12/861,106, filed on Aug. 23, 2010, now U.S. Pat. No. 9,363,880 which is a continuation-in-part of U.S. application Ser. No. 12/726,097, filed on Mar. 17, 2010 (now abandoned), which claims the benefit of U.S. provisional application Ser. 61/162,785 filed on Mar. 24, 2009 and U.S. provisional application Ser. 61/306,774 filed on Feb. 22, 2010, all of which are incorporated herein by reference.

STATEMENT REGARDING FEDERALLY SPONSORED RESEARCH OR DEVELOPMENT

This invention was made with government support under 58-1935-6-647 awarded by U.S. Department of Agriculture/Agriculture Research Service. The government has certain rights in the invention.

TECHNICAL FIELD

The present application relates an apparatus and method for treating packaged products to reduce undesirable contamination. More, specifically a system and method of reducing the level of organisms which may be related to deterioration of the product or to human pathology is described.

BACKGROUND

Recent trends in dieting and healthy eating have shown a high demand for fresh produce. According to USDA Economic Research Service statistics, fresh spinach, for example, reached a record consumption in 2005 with 738 million pounds in the United States: more than 12 times the amount consumed in 1970. Processed spinach consumption, conversely, has tended to decline over the last few decades. This high demand for fresh, nutritious produce puts pressure on producers and processors to ensure that products are safe for human consumption, yet continue to retain expected nutritious and aesthetic qualities. Minimal processing and treatment appears desirable in order to maintain the fresh taste, texture, and nutrition of produce. However, many sources of contamination exist that can affect produce before, during, and after harvesting. Sources of contamination include fecal matter from animals, both wild and domestic, contaminated irrigation water, flooding of crops, as well as from personnel involved with handling of products Due to the specific growth conditions of produce, particular varieties are not always in season locally, and are often shipped from all parts of the nation and world to meet the demands of consumers. Many aspects of shipping can cause a decrease in the quality of fresh produce. Spoilage could occur from, for example, unsanitary transportation vehicles, lengthy shipping schedules, and improper storage temperatures and ventilation of storage areas. Conventional methods of sanitizing fresh produce involve various washing procedures. More efficient processing methods are needed to reduce the risk of contaminated produce, while still maintaining its fresh qualities.

Atmospheric, non-equilibrium plasma (ANEP) is an example of a non-thermal processing method. There is a wide variance in the terminology for the process to produce such a plasma. In the literature, a variety of terminology is used to describe the phenomenon including atmospheric glow discharge, surface barrier discharge (SBD), dielectric barrier discharge (DBD), Single Dielectric Barrier Discharge (SDBD) and Surface Plasma Chemistry Process (SPCP). For convenience herein, the term dielectric barrier discharge (DBD) is used, without intending to exclude any of the ANEP plasma generating mechanisms implied by choosing a specific terminology for description of the technique herein.

FIG. 1 shows simplified examples of DBD configurations that may be used to produce an ANEP in an ambient air environment. A high voltage generator 10 applies an alternating current potential to a pair of metallic plates 20, 30, spaced apart from each other to form a region 50 in which an object may be placed. At least one dielectric layer 40 is disposed between a first plate 20 and the second plate 30. In this manner, the effect of the dielectric layer is to limit the current of any filamentary discharge that is formed between the plate 20, 30 so as to prevent the formation of a high current arc. The discharge in region 50 is thus limited in energy and results in an ANEP where variety of reactive species may be formed from the $O_2$, $N_2$ and possibly water vapor. FIG. 1A shows a configuration with one dielectric layer 40 laid against an electrode 20. FIG. 1B shows an example where a dielectric plate 40 is laid against an electrode 20 and another dielectric plate 60 is laid against a second electrode 30. The charge accumulation on the plates, which may be used in conjunction with the voltage waveform, to estimate the power consumption, may be measured by determining the voltage developed across a conventional capacitor 75. FIG. 1C illustrates a situation where a single dielectric layer 50 is disposed between the electrodes 20, 30, so that two regions 50 are formed in which an ANEP may be formed.

As the possibility of an arc forming directly between the plates 20, 30 exists, by air paths around the dielectric, at least one electrode is often fully enclosed in an insulating material, and the exposed electrode may be grounded. The insulating material may be the same material as used for the dielectric 40, 60 however the two materials may have differing properties. For example, the dielectric plate may be quartz, and the insulating material may be a moldable material.

The food industry is always seeking a better method for maintaining food safety and ozone treatment may be an effective possibility due to its antimicrobial properties and lack of residual substances. However, ensuring minimal to no exposure of employees to ozone is a concern. Similar considerations would apply to the medical field, where sterilizing packaged objects and maintaining sterile conditions is important.

SUMMARY

A system and method are described where reactive species may be produced by an atmospheric non-equilibrium plasma (ANEP) in a closed package containing an object to be decontaminated, so as to suppress or eliminate contaminants. The reactive species may be of a short lifetime so as to perform the treatment during a period of time during and shortly after a discharge creating the plasma. Longer lifetime species may remain so as to perform, or to continue to perform, the treatment for an extended period of time. Eventually, the reactive species may be eliminated from the treatment volume by reacting with the contents of the package, the package, or with each other. As the reactive species may be contained within the package, exposure of personnel to such reactive species may be minimized.

The package may form a storage space for a product, which may be, for example, a food product, or a medical device, which may remain inside the package during and after treatment. The package may also contain a working gas fill, which may be air, or a mixture of gases, which may include noble gases. An atmospheric non-equilibrium plasma (ANEP) is produced within the package by a voltage gradient applied from outside the package. By selecting the working gas mixture, the duration of the ANEP creation, and the duration of the treatment, the treated product may have reduced contamination, or be sterilized, depending on the specific application. The working gas mixture, the equipment geometry and the operation voltage are selected so that the electrodes may be situated in the ambient manufacturing environment and produce reactive species within the package, while avoiding or minimizing the production of such species outside of the package.

A system for treating a product is described that uses an apparatus configured to create a reactive species in a part of a package or storage volume sized and dimensioned to contain an object to be treated. The object to be treated is stored within the storage volume.

In an aspect, a system for treating a product is described, having an apparatus configured to create a atmospheric non-equilibrium plasma (ANEP) in a working gas in a storage volume sized, and dimensioned to contain an object to be treated.

The working gas includes a noble gas in a percentage sufficient to reduce a voltage gradient needed to create the ANEP.

In another aspect, a method of decontaminating an object includes the steps of providing a dielectric barrier discharge (DBD) device; providing a container suitable for substantially completely enclosing the object and a working gas; inserting the object into the container; disposing at least a portion of the container such that reactive species may be produced in the container by the DPD apparatus; and activating the DBD device.

DETAILED DESCRIPTION

Figure 1A:
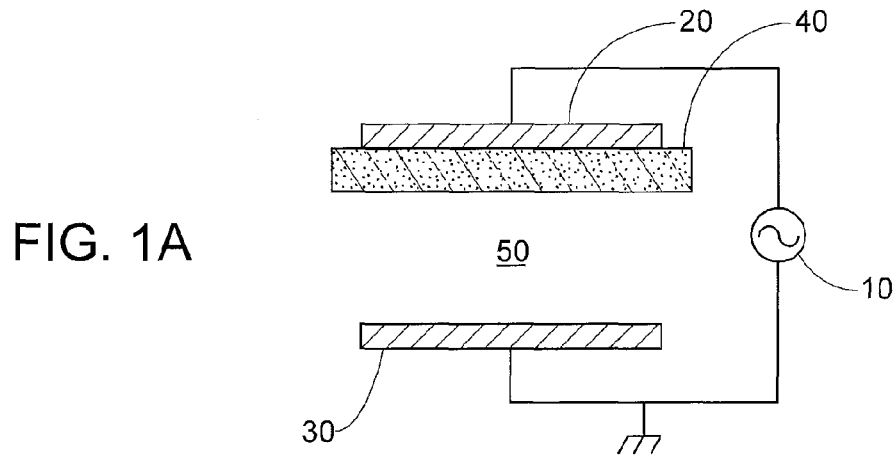
FIG. 1 (prior art) shows (A) a DBD apparatus having a single dielectric barrier; (B) a DBD apparatus having two dielectric barriers and an auxiliary capacitor for measuring the DBD charge; and, (C) a DBD apparatus with the dielectric disposed between two conducting plates.
Figure 1B:
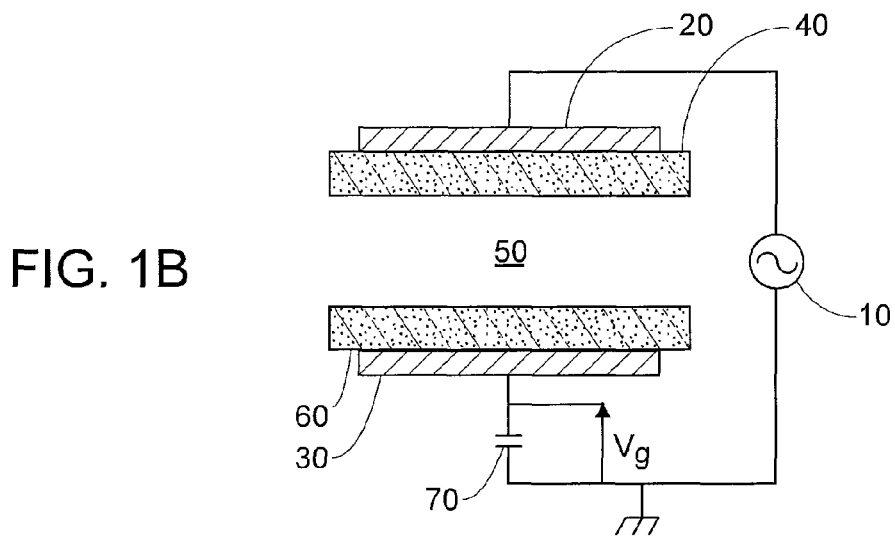
Figure 1C:
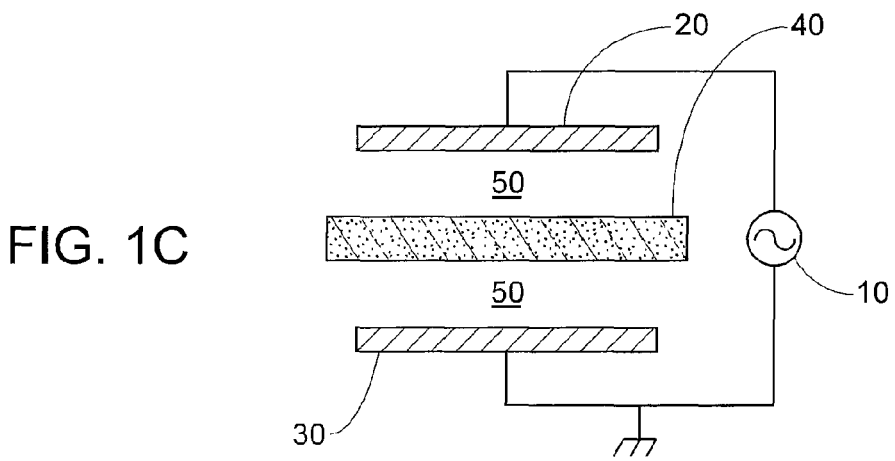

Exemplary embodiments may be better understood with reference to the drawings, but these examples are not intended to be of a limiting nature. Like numbered or labeled elements in the same or different drawings perform equivalent functions. When a specific feature, structure, or characteristic is described in connection with an example, it will be understood that one skilled in the art may effect such feature, structure, or characteristic in connection with other examples, whether or not explicitly stated herein.

It will of course be appreciated that in the development of any such actual implementation, numerous implementation-specific decisions must be made to achieve specific development goals, such as compliance with system and business related constraints, and that these goals will vary from one implementation to another. Moreover, it will be appreciated that such a development effort might be complex and time-consuming, but would nevertheless be a routine undertaking of engineering for those of ordinary skill in the art having the benefit of this disclosure.

Atmospheric pressure "cold" plasmas have been shown to be effective in reducing or eliminating surface bacterial contamination of food samples. The term "cold plasma" is meant to describe a plasma discharge, which may be a non-equilibrium plasma, occurring at a pressure of about one-atmosphere and at near ambient temperature (ANEP). This is to distinguish the ANEP plasma from a thermal plasma discharge operating at a bulk gas temperature of hundreds or thousands of degrees above the ambient temperature. In an atmospheric pressure "cold plasma" the electrons may have a significantly higher temperature than the ion and neutral species; however, the bulk temperature of the working gas is not significantly raised. In this context, however, the term "cold" should not be interpreted to require refrigeration or other cooling to perform the decontamination or treatment functions described herein; however, this does not exclude the treating or the subsequent storage of the treated object at an appropriate temperature, which may include refrigeration or cooling. Keeping the gas at a near-ambient temperature may contribute to avoidance of heat damage to the sample being treated.

One technique of creating a non-equilibrium plasma is to apply a high voltage to the volume to be ionized, while inhibiting the transition from a glow discharge to an arc discharge by limiting the discharge current. This may be done, for example, by covering at least one of the electrodes of the apparatus with a dielectric layer; resistive layers have also been used. The discharge current is self-limited by charge build up on the dielectric surface. Typically, the excitation voltage frequency is in the kHz range, but may range from power line frequencies to radio frequencies. The experimental data presented herein used a 60 Hz frequency due to the availability of high voltage transformers, whose voltage could be easily be adjusted by controlling the input voltage thereof with a variable voltage transformer.

Dielectric-barrier discharges (DBD) are a type of alternating-current high-voltage gaseous discharges that may be formed in a nominally atmospheric pressure environment. The presence of a dielectric layer between the electrodes prevents the charges generated in the gas by the discharge from reaching at least one of the conducting electrode surfaces. Often the dielectric layer is applied to both of the electrodes. Within each half-cycle of the driving voltage waveform, when the voltage gradient applied across the gas exceeds that required for breakdown, the formation of narrow ionized discharge filaments initiates the conduction of electrons toward the more positive electrode, and ions towards the more negative electrode, although the mobility of the electrons is greater. Electrical charge accumulates on the dielectric layer(s) at the end(s) of each ionized filament, and the voltage drop across the ionized filament reduces until the voltage falls below the discharge-sustaining level, so that the discharge is extinguished. The duration of the filamentary discharge is believed to be quite short: of the order of 100 nanoseconds or less. However, the resultant reactive species may have a significantly longer lifetime. The low charge mobility along the surface of the dielectric also limits the lateral region over which the gap voltage is diminished, so that a plurality of filaments may form in close proximity to one another.

Production of ozone in a DBD occurs between the two electrodes when operated at a particular voltage, frequency, and geometry. In air, mixtures of $O_2$ and $N_2$, or $O_2$ alone, reactive oxygen species are generated which react with each other as well as oxygen molecules resulting in the formation of ozone. Other reactive species are created when $N_2$, or other gases such as $CO_2$, $H_2O$ or Cl are present. The most oxidative species in air and oxygen gas include ozone ($O_3$), singlet oxygen (O or $O^-$), superoxide ($O_2^-$), peroxide ($O_2^{-2}$ or $H_2O_2$), and hydroxyl radicals (OH). Most of these species have very short half-lives (in the range of milliseconds); however, ozone has a much longer half-life ranging from minutes to days depending on conditions. The effects of gaseous ozone on foods has previously been studied with promising results and ozone has been shown to be more efficient at lower concentrations and treatment times than more standard sanitizers, including chlorine. The use of ozone has been limited to the treatment of unpackaged products.

Plasma-generated species may be capable of reacting readily with various materials and organisms. Oxygen- and nitrogen-based reactive species are effective in the inactivation of microorganisms and may include ozone ($O_3$) and nitric oxide (NO). For example, *E. coli* O157:H7 on lettuce was shown to be reduced by 1.79 $\log_{10}$ (CFU/g) (colony-forming units per gram) after 15 min of treatment with gaseous ozone. Similar reductions of *E. coli* O157:H7 and *Salmonella enterica* inoculated on blueberries have been reported. A number of researchers were able to inactivate various food-borne pathogens in unpackaged samples using assorted plasma systems with treatment times ranging from seconds to minutes on fresh produce surfaces including apples, cantaloupes, and lettuce. After production thereof, reaction products of an ANEP may have the ability to decompose or recombine, leaving no residual chemicals or reactive species.

Many examples of the creation of such plasmas are in flowing gases or in the ambient environment. However, such plasmas quickly dissipate or are transported away from the sample to be treated by air currents or pressure differentials. Here, an apparatus and method for localizing the ionized and other reactive species that are created is described, so that the treatment time may be extended and the ionized and other reactive species confined to the neighborhood of the object being treated.

In particular, the object to be treated may be enclosed in a sealed or substantially sealed container. The container need not be hermetic unless the level of decontamination desired is such that subsequent contamination from another source is to be avoided. Non-hermetic containers may be used in applications where subsequent re-contamination of the sample is prevented by the characteristics of the packaging. Non-hermetic containers may be permeable to some extent to air, and to the other constituent gases or the radicals or reactive species produced in the ANEP. That is, the packaging may be porous to gases, but prevent spoilage or pathogentic material from entering the package. The composition of the container may be a plastic such as TYGON, low-density polyethylene (LDPE), high density polyethylene (HDPE), polyethylene terapthalate (PET), or polystyrene; however, various other substantially dielectric materials can be used, including, glass, wax, cardboard, paper, foil, eggshells, low dielectric constant materials, or the like. The foil may be a plastic having a thin metallic coating. This may permit the treatment of objects stored in a foil package, or having a foil liner.

The system and method described herein may achieve at least 1-3 $\log_{10}$ reductions of spoilage organisms and greater than 5 $\log_{10}$ reductions (total kill for oxygen working gas at room temperature and refrigeration after 24 hr storage) of *E. coli* O157:H7 in fresh produce with minimal quality changes in seconds to minutes of active treatment. The amount of contaminant reduction needed depends on the specific product to be treated, the subsequent storage conditions, storage time and similar considerations, which will often be governed by economic and regulatory factors. While the studies described herein are related to bacteria, similar effects should be experienced for fungi and virus contaminants.

An apparatus for treating a sample is shown in FIG. 2. An object to be treated 200 is placed in a substantially closed dielectric container 100. The container may be rigid or flexible and may be sealed by a ZIPLOC closure, by heat, by a close-fitting cap, or any other mechanism that has a similar effect. The container should have an ability to substantially retain the reactive species that are the residual of the generated ANEP plasma for a period of time that is sufficient for a particular treatment process. The working gas, which may be air, or a modified atmosphere packaging (MAP) mixture, may be introduced into the container 100 prior to treatment. The container 100 may be purged prior to charging with the working gas so as to control the resulting gas mixture. The container may be sealed either permanently or temporarily prior to treatment.

A region within the container is selected where an ANEP may be generated. This may be a specific formed region of a semi-rigid or rigid container, or may be formed by manipulation of a flexible container where the gas pressure gives the container a deformable shape. In rigid containers, the gas pressure may be less than an atmosphere, while the gas pressure in a flexible container is an atmosphere or greater. This does not exclude situations, for example, where vacuum packing is used, and a working gas may be introduced for the purposes of the treatment.

Figure 2A:
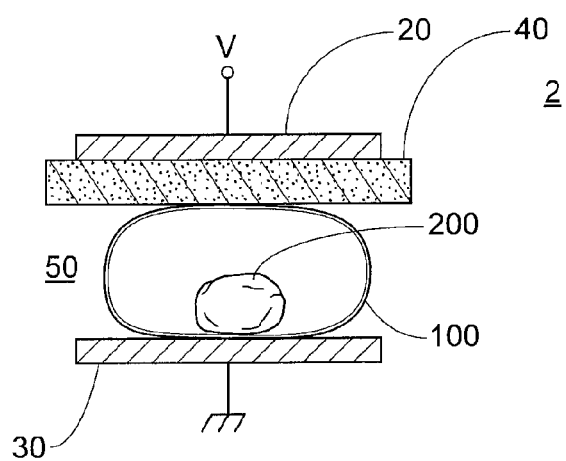
FIG. 2 shows (A) a portion of a DBD apparatus where a container having an object to be treated disposed between the plates of the apparatus; (B), a portion of a DBD apparatus where a container having an object to be treated is disposed between the plates of the apparatus, such that the object to be treated is not disposed between the plates of the apparatus; and, (C) a top view of a portion of the apparatus of FIG. 2A.
Figure 2B:
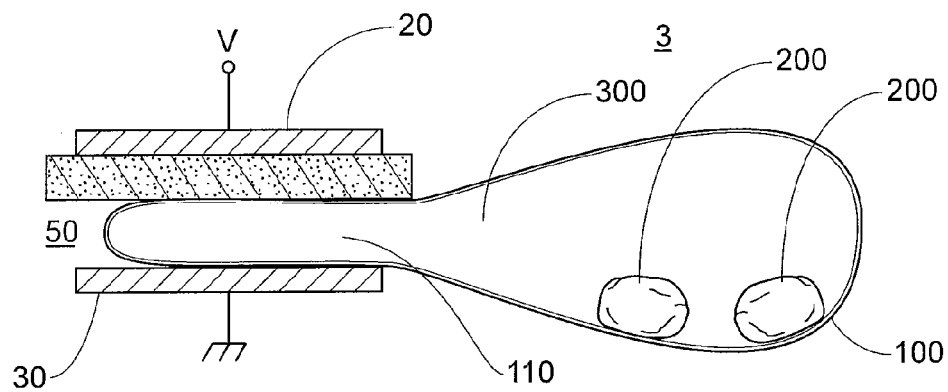

FIG. 2A illustrates a situation where the object being treated is disposed between the plates of the apparatus, while FIG. 2B illustrates the situation where the object being treated is disposed so that a small thickness of the storage bag having a gap between the opposing surfaces is disposed between the plates of the apparatus. For the situation of FIG. 2B, the ANEP is created inside a portion of the storage container; however, the object to be treated may not be directly exposed to the active ANEP. Rather, the residual reactive species may be diffused or circulated to the volume of container having the object to be treated. This configuration reduces the voltage needed to establish the ANEP as the distance between the electrodes has been reduced compared with the thickness of the object. In addition, where the termination of the plasma filaments on the object itself may be undesirable, that situation is avoided.

In contrast, the arrangement of FIG. 2A disposes the object to be treated between the electrodes, and the object itself may behave as a dielectric, similar to that used on one or more of the electrodes. In this circumstance, the filaments creating the ANEP may extend from the electrode or the dielectric barrier on an electrode, or an electrode without a dielectric barrier, to a surface of the object to be treated, and an active ANEP may also surround the object. The electrons and the ions created in the ANEP may directly impinge on the surface of the object. Similarly to the arrangement of FIG. 2B, the object may continue to be exposed to the ANEP byproducts after the active phase of ANEP generation has been completed. Each of the processes may be repeated, if needed, where the object or the storage bag is manipulated to better distribute the active byproducts or expose other portions of the object to the plasma.

As shown in FIG. 2A, the container 100 having a working gas 300 and an object to be treated 200 may be disposed between the plates of a DBD apparatus 2. The plates 20, 30 are spaced apart so as to admit at least portion of the container 100 containing the object to be treated 200. The distance between the plates may be controlled by mechanical means so that the container 100 may conveniently be placed between the plates 20, 30, and the spacing between the plates subsequently adjusted so as to partially compress the container 100, so as to achieve an appropriate gap spacing for the creation of the ANEP within the container 100. In this configuration, filamentary discharges may occur between the dielectric surface 40 of the top plate 20 and the opposing surface of the object 200 being treated, and may also occur between the bottom plate 30 and the object being treated 200. The ANEP may also be created by electrical currents flowing directly from one plate to another, as mediated by the dielectric layer on the plate.

Where the object to be treated has the general characteristics of a dielectric material, the filaments will have a behavior similar to that which would occur in a DBD apparatus without an introduced object, except that the filaments may terminate one end thereof on the object. So, the object will be directly exposed to the filamentary discharges creating the ANEP, as well as to the shorter lasting and longer lasting reactive species that are created during the active treatment phase. As the surface density of filaments is governed by the electrical field distribution, and the shape and electrical properties of the object to be treated, the entire surface of the object may not be subject to the same intensity of direct treatment. Should more uniform treatment be desired, the object to be treated 200 may be manipulated to expose other parts of the object to direct treatment.

The high voltage is often sinusoidal and may be produced by a high-voltage transformer connected to the power grid, a signal generator connected to an amplifier, or the like. For the experiments described herein, a maximum voltage of about 18 KV (RMS) was used, however informal experiments are being performed using a higher voltage of about 75 KV, with an objective on exploring the range up to about 120 KV. In experiments performed at about 65 KV, with the same gap as used at lower voltages, the rate generation of reactive species appears to substantially faster, with about the same concentration of reactive being achieved after 15 seconds as was observed after 5 minutes at about 15 KV.

Other voltage waveform shapes may be used, including sawtooth, trapezoidal, or pulsed, and the voltage waveform may be symmetrical, asymmetrical, or displaced from DC.

The amplitude of the voltage may be controlled during operation of the apparatus by, for example a VARIAC transformer, or by controlling the signal generator amplitude output, or the amplifier gain. The frequency of operation may be fixed or variable. ANEP plasmas have been created using frequencies ranging from DC (where a resistive layer is used a current limiter or ballast) to radio frequencies (RF). In the experiments described herein, the local power line frequency (60 Hz) was used for convenience in configuring the experimental apparatus and cost considerations.

The voltage gradient at which a glow discharge is formed is a function of the constitutive gases present between the electrodes, various geometrical considerations, and the gas pressure. For most of the experimental data presented herein, a simple ambient air mixture or pure oxygen was used. For purposes of visualization of the filamentary discharges, pure helium (He) was sometimes used due to the substantially lower ionization potential and to produce a clearly visible glow in the ionized region and on the dielectric surfaces. The constituent gases may be modified so as to achieve a desired concentration and species of ionized particles. In addition to air, $O_2$, $N_2$, $CO_2$, $H_2O$, Cl, and other mixtures, or pure gases, including inert and noble gases, are usable, depending on the application.

As shown in FIG. 2B when a flexible container 100, which may be a plastic storage bag, is used, the internal gas pressure may selected so a that a portion of the container may be compressed between the plates 20, 30 so as to form a smaller gap to facilitate creation of the ANEP at a lower voltage. Here, the container is shown in a state where a portion 110 of the container 100 is positioned between the electrodes of the DBD apparatus 3, so that a portion of the container 100 may be temporarily formed into a region where the ANEP may be created. The filaments creating the ANEP are formed between the surface of the dielectric 40 and the other electrode plate 30, such that there the object 200 to be treated is not disposed therebetween. In this manner, larger objects may be treated without having to use very high voltages. Portions of the container surface disposed so as to form the region in which the ANEP is to be formed are held against the dielectric 40 and the plate 30 by the internal gas pressure. The effect of the dielectric layer of the container surface may be small, as the charge distributions are likely to be dominated by those of the electrodes and the dielectric 40.

Figure 2C:
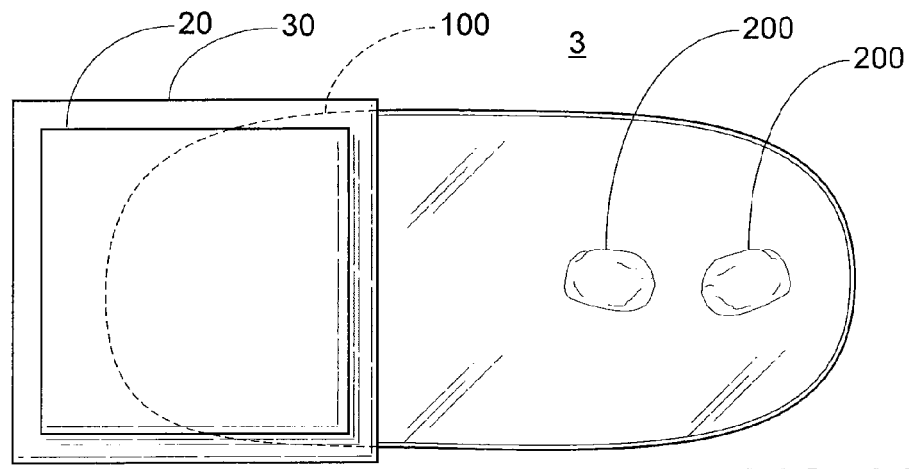

FIG. 2C shows a top view of the DBD apparatus 3 of FIG. 2B. The dielectric material extends so as to inhibit stray discharges, and the electrodes are disposed opposite only a portion of the storage volume.

The electrodes may be planar, as shown; however, other geometries may be used to conform to a container such as a box, pill bottle, jar, or other shape. Shaped electrodes may be used to encourage the formation of a plasma jet, or better distribute the reaction products using induced convection. For example, large cardboard containers may be processed by using a pair of electrodes oriented at a 90° angle and placed along one or more of the edges. Similar configuration may be used for large packages of other materials and shapes.

The effects of ANEP treatment of packaged produce was studied using, fresh, bagged spinach and chicken. Spinach was chosen due to its popularity as a fresh health food, yet subject to recent outbreaks of *E. coli* O157:H7 found on packaged spinach leaves. Leaves of packaged spinach were treated in plastic food storage bags containing one of two different gases and stored at two different temperatures. The effectiveness of in-package ANEP treatment in suppressing spoilage organisms and *E. coli* O157:H7 was tested, as well as the effects of treatment and storage on quality of spinach leaves.

The spinach used in the experiments was obtained from a local supermarket in West Lafayette, Ind. The spinach had been cut and bagged, and was stored under refrigeration in the supermarket. The same brand of spinach was used for each test (Dole Food Co., Thousand Oaks, Calif.). Full-sized spinach leaves were used for spoilage organism tests while baby spinach leaves were used for *E. coli* O157:H7 tests. The average surface area of leaves used for spoilage organism tests was 56.2 cm2. The average weight of leaves used for *E. coli* O157:H7 tests was 0.570 g. All bags were stored at 5° C. after purchase and were used in the experiment prior to the expiration date listed on the outside of the bag. An unopened bag of spinach was used as the source of spinach leaves for each test.

Prior to treatment, spinach leaves of visually similar surface area were selected from the bag. Leaves were weighed and placed on aseptic wax paper and an outline tracing made for subsequent determination of leaf surface area.

Clear, 3.78 L storage bags were obtained from a local grocery store in West Lafayette, Ind. Two different brands were used throughout the course of the spinach experiment: Great Value Food Storage Bags (Great Value, Walmart, Bentonville, Ark.) and Glad Food Storage Bags (The Glad Products Company, Oakland, Calif.). The bags are believed to be fabricated from low-density polyethylene (LDPE) and were 1.6-mm thick. It is known that storage of spinach leaves in a controlled atmosphere (CA) of 7-10% $O_2$ and 5-10% $CO_2$ delays discoloration; however, plastic films used for commercial packaging are usually chosen to maintain an environment of 1-3% $O_2$ and 8-10% $CO_2$. Retail zip-top bags were chosen as the dielectric material for the ozone treatment experiments of spinach, as only one of two gases would be used in each bag for this study: either air or oxygen. The retail bags were low cost, easy-to use, and were sufficient for proof-of-concept of an in-package treatment. Other bag technologies and materials may be used, depending on costs, storage duration, storage conditions, or the like.

The values of leaf surface area were then used to determine the CFU/cm$^2$ of each leaf. The average population of spoilage organisms on the spinach leaves prior to treatment was 3.19 $\log_{10}$ (CFU/cm$^2$). After tracing, leaves were placed on aseptic stands that were designed to allow plasma exposure on both sides of the leaves during treatment and storage. The stands were then placed inside individual sterile, re-sealable, polyethylene bags, each bag containing a single spinach leaf.

A single strain of *E. coli* O157:H7 (6460) was used for the evaluation of the ANEP treatments. The strain was obtained from Dr. R. H. Linton of the Food Science Department at Purdue University, West Lafayette, Ind. Cultures of the bacteria were grown in trypticase soy broth (TSB) and placed in a shaking incubator for 18 h at 37° C. Spinach leaves were weighed and placed in sterile petri dishes prior to inoculation. Each spinach sample was spot inoculated (8-10 spots) with 100 μL of the *E. coli* culture and placed in a biosafety hood for 1 h to allow for bacterial attachment. The average population of control samples was 5.40 $\log_{10}$ (CFU/mL).

The oxygen content in each bag was measured before treatment and after storage using a gas analyzer (MOCON, Inc., Minneapolis, Minn.). The analyzer had a syringe connected to a tube which fed to the analyzer. The syringe tip was placed inside the bag through the re-sealable opening (bags were not punctured) to measure the gas inside. Two readings were taken during each measurement to ensure values were accurate.

The temperature of the surfaces of the leaves and the electrodes was measured and recorded just prior to, and just after, treatment with an infrared thermometer (Omega Engineering, Inc., Stamford, Conn.).

The relative humidity inside storage bags containing a single spinach leaf was measured. A single, un-inoculated spinach leaf and a relative humidity sensor (Thermo-Hygro Control Co., Friendswood, Tex.) were placed inside the storage bag. The bag was then filled with either air or oxygen gas as before. The relative humidity was recorded before and after the 5 min treatment or storage. Relative humidity tests were replicated 10 times for air and oxygen and treated and untreated samples.

The treatment system used operated at a frequency of 60 Hz generating about 12 kV of potential between the electrodes, and the power consumption was 40 W. The voltages for all experiments were measured with a conventional voltmeter, yielding RMS voltage values. The electrodes were made of coils of insulated wire wound around a planar dielectric form with a treatment area of about 51 cm$^2$ (8.5 cm by 6 cm). Treatment of all samples occurred at ambient laboratory temperature (nominally 22° C.).

Bags containing the samples were filled with the working gas (air or oxygen for this example) and purged three times to ensure purity of the gas in the bag, which was verified with the gas analyzer. A small amount of gas was expelled from the bag to allow for orientation of plasma electrodes. The electrodes were placed above and below the bag, oriented on top of each other. The bag in between the electrodes had an approximate gap distance of 3-3.5 mm, which permitted formation of an ANEP with the available voltage. The system was then activated for a 5-min active treatment period.

The gas in the bag was agitated manually, once during each minute of treatment, for about 10-15 s, to allow for a more uniform distribution of gas inside the bag. This was done by pressing lightly back-and-forth on the bag so as minimize the change in the alignment of the electrodes or disturb the sample. The bag was then placed in a stable location at either room temperature (22° C.) or refrigeration (5° C.) for a predetermined storage period (0.5, 2, or 24 h).

After storage for the specified time, the ozone and/or nitrous oxide content was measured by means of DRAEGER Short-Term Detector tubes (Draeger Safety AG & Co. KGaA, Luebeck, Germany). Tubes (specific to measuring ozone) of two different scales were used to measure ozone concentration, 0.05-0.7 ppm and 20-300 ppm ozone for volumes of 100 mL. One type of tube (specific for measuring nitrous oxides) was used for determining nitrous oxide concentration. This tube had two scales depending on the volume drawn through the tube. Scales ranged between 2-50 ppm and 5-100 ppm for volumes of 500 mL and 1000 mL. In order to determine concentration values when measuring very high concentrations of species, the tubes were connected to syringes by means of flexible tubing. Volumes of gas were drawn through tubes and estimates of actual concentrations were determined by comparing the ratio of values of measured concentration and volume to actual concentration and volume, and solving for the actual concentration.

Measurement of these gases gave approximate concentrations. The detector tubes had accuracies off 10% to +15%.

Also, the nitrous oxide tubes had cross sensitivities with ozone making for less accurate results for the nitrous oxide concentrations.

Following storage, the leaves were aseptically removed from bags and placed in 100 mL of 0.1% peptone water. Leaves were stomached for 2 min on high to remove microbes from the leaf surface. Serial dilutions were then performed using standard procedures for microbial recovery and 0.1 mL samples were surface-plated on plate count agar (PCA) for spoilage organisms, and Sorbitol-MacConkey Agar with Cefixime-Tellurite (CTSMAC) for $E.$ $coli$ O157:H7. All samples were incubated at 37° C. for 24 h. Survivors were counted after incubation and recorded as $\log_{10}$ (CFU/cm$^2$) for spoilage organisms and log 10 (CFU/mL) for $E.$ $coli$ O157:H7.

Microorganism reductions observed for all treatments are listed in Table 1. The results from the treatment of spoilage organisms showed multiple log 10 reductions in populations for most treatments, with the exception of the samples treated in air-based ANEP and stored for 24 h at room temperature (22° C.). In this case, after 24 h of storage the level of spoilage organisms actually increased by 0.77 $\log_{10}$ (CFU/cm$^2$) when compared with the initial population of spoilage organisms on control samples. The increase in population of this sample after storage is believed to be due to organisms which survived treatment and the effects of remaining ANEP species, e.g., the ozone and nitrous oxides, during storage and subsequently grew at room temperature. This may suggest that the air ANEP treatment prior to refrigeration of samples would need adjustment of the treatment conditions from those used in the experiment as any surviving spoilage organisms could potentially increase in population between treatment and refrigeration. However, samples treated with air and oxygen ANEP and stored under refrigerated conditions showed multiple $\log_{10}$ reductions (2.47 and 3.55 $\log_{10}$ for air and oxygen ANEP, respectively) as indicated in Table 1.

Oxygen ANEP showed increased effectiveness at reducing spoilage organisms when compared with ANEP generated with air. The increased bactericidal effect from oxygen ANEP is believed to be caused by the increased levels of ozone generated. So, a longer treatment time in air or a more intense phase of ozone generation may be indicated for treatment of spoilage microorganisms. The bactericidal effects at these levels for the other treatment cases could increase shelf-life of produce if the produce was refrigerated immediately after treatment, allowing for fresh products to be shipped further and potentially last longer in the homes of consumers.

TABLE 1

Measured parameters of spinach leaves before and after treatment and storage.

| Plasma Gas Type | Storage Temp ° C. | Storage Time hr | Pre Treatment Leaf Temp ° C. | Post Treatment Leaf Temp ° C. | Spoilage Organism Reductions $\log_{10}$(CFU/cm$^2$) | $E.$ $coli$ O157:H7 Reductions $\log_{10}$(CFU/mL) | Post Treatment Ozone ppm | Post Storage Ozone ppm | Plasma Gas Type | Post Storage Oxides ppm |
|---|---|---|---|---|---|---|---|---|---|---|
|  |  | 0.5 |  |  | — | 0.80 |  | 450 |  | 150 |
| Air | 22 | 2 | 22.2 | 22.3 | — | 1.86 | 650 | 70 | 460 | 40 |
|  |  | 24 |  |  | −0.77* | — |  | 0 |  | 0 |
|  |  | 0.5 |  |  | — | 0.20 |  | 320 |  | 315 |
| Air | 5 | 2 | 21.6 | 21.7 | — | 1.47 | 650 | 100 | 460 | 65 |
|  |  | 24 |  |  | 2.47 | 4.32$^a$ |  | 0 |  | 0 |
|  |  | 0.5 |  |  | — | 0.34 |  | 1480 |  | — |
| Oxygen | 22 | 2 | 22.0 | 22.2 | — | 3.53 | 1730 | 800 | — | — |
|  |  | 24 |  |  | 3.50 | 5.25**,$^a$ |  | 0 |  | — |
|  |  | 0.5 |  |  | — | 0.66 |  | 780 |  | — |
| Oxygen | 5 | 2 | 21.6 | 21.8 | — | 2.99 | 1730 | 130 | — | — |
|  |  | 24 |  |  | 3.55 | 5.75**,$^a$ |  | 0 |  | — |

*Increase in organism population.
**Indicates no survivors enumerated after incubation.
$^a$Indicates that these values are not statistically different.

All of the treated leaf samples inoculated with $E.$ $coli$ O157:H7 showed reductions in populations following storage. The reductions of $E.$ $coli$ O157:H7 treated in both air and oxygen ANEP increased as storage time increased. This may suggest the long-acting effect of the confined reactive products. Multiple storage times (0.5, 2, and 24 h) were used to obtain data to ascertain when a total kill of the pathogen occurred. As evidenced in Table 1, multiple $\log_{10}$ reductions were indicated after 2 h storages for all samples. Samples treated with ANEP containing oxygen as the gas present, and stored for 24 h, showed no surviving $E.$ $coli$ O157:H7 organisms. Further testing is being performed for 24 h room temperature storage data for samples treated with air ANEP.

Samples treated with oxygen as the gas for ANEP generation showed increased log 10 reductions for most samples when compared with samples treated in air, with the exception of samples stored at room temperature with oxygen ANEP (0.34 log 10 reduction). Again, the increased effectiveness of ANEP generated in oxygen gas fill is believed to be due to the increased concentration of ozone produced during treatment. This data suggests that produce potentially contaminated with $E.$ $coli$ O157:H7 could effectively treated to eliminate the pathogen before the produce arrives at the grocery store or market.

All the leaves were at room temperature just before treatment (between 21° C. and 22° C.). The sample temperatures did increase slightly after treatment however this increase was, on average, in the range of 0.1° C.-0.2° C. This data suggests that the treatment was effectively non-thermal and that the reductions in CFU were due to generated plasma species and the storage temperatures (room temperature and refrigeration). The average temperature of the ANEP electrodes before and after 5 min of treatment was 27.0° C. and 50.3° C., respectively. This is an average increase of approximately 23° C. for the electrodes. The heating of the electrodes may be reduced by cooling and other design measures in an industrial application.

The measured species generated in air-based ANEP include ozone and nitrous oxides, while only ozone was measured for oxygen-based ANEP. Ozone and nitrous oxides were the two most readily measurable species produced during ANEP treatment. A 5 min treatment with the ANEP system produced very high levels of both species, particularly ozone. Oxygen-based ANEP produced an average of 1730 ppm ozone and air-based ANEP produced averages of 650 ppm and 460 ppm for ozone and nitrous oxides, respectively, immediately after treatment. These species decreased in concentration during the storage period, eventually reaching an undetectable or zero level, leaving no residual species after 24 h of storage, as indicated in Table 1. The data obtained indicates that oxygen ANEP produces, on average, substantially higher concentrations of ozone than air ANEP. This is apparently due to the initial concentration of oxygen in the base gas, oxygen gas being 100% oxygen and air containing only 21% oxygen. Despite the wide range of results with the current measurement method, it is still evident from the resulting reductions of spoilage organisms and E. coli O157:H7 as well as the discoloration of leaves, that the pure oxygen ANEP system consistently produces high levels of oxidative reactive species.

All of the test conditions showed no detectable ozone after 24 h of storage, suggesting that measurable ozone had either decayed to a neutral gas, or had reacted with the test samples inside the package, with the package itself, or had diffused through the package material. The rate of decay of ozone for each set of temperature and gas type conditions was calculated by plotting ozone concentrations at storage times of 0, 0.5, and 2 h and fitting an exponential curve to the data points. Half-lives were calculated from the resulting fitted exponential equation. Calculated half-lives for ozone generated in oxygen and stored at room temperature and refrigeration were 78 and 87 min, respectively. Half-lives for ozone generated in air and stored at room temperature and refrigeration were 160 and 99 min, respectively. When measured ozone levels were compared between temperatures for each gas there was no significant difference ($P<0.05$) between refrigerated and room temperature concentrations at each storage period suggesting that the calculated half-lives may not significantly different.

A follow-up study was conducted to assess the affect of water presence on half-lives of ozone in the plastic bags utilized for treatments. Bags were filled with air or oxygen only or air or oxygen and 1 g of liquid water. Samples were actively treated for 5 min with the experimental system and stored for 0, 2, 4, and 24 h at room temperature (RT) (22° C.) and refrigeration (5° C.). Ozone concentrations were measured and half-lives were calculated as before. The half-lives of ozone were longer in all refrigerated samples when compared with samples stored at room temperature. The presence of nitrogen in air during the generation of ozone may also produce reactive nitrogen species (RNS) such as NO. These RNS species could cause different reaction pathways between the E. coli O157:H7, the spinach leaves, and the package, than the reaction pathways in pure oxygen, under the same conditions, and during the storage period.

The color of spinach leaves was assessed visually after treatment/storage. A rank number was assigned to each leaf evaluated indicating the relative percentage of leaf area that had been discolored after storage. The scale used ranged from 1-5, with 5 being the best quality (no discoloration) and 1 being the worst (entire leaf was discolored). The experimentally determined values were averaged and are presented in Table 2.

TABLE 2

Average values of appearance of discoloration on spinach leaves after various storage times.

| Storage, h | Air, RT | Air, Ref | O2, RT | O2, Ref |
|---|---|---|---|---|
| 0.5 | a | 4.8 | 4.6 | 3.0 |
| 2 | a | 4.3 | 3.0 | 1.7 |
| 24 | 1.3 | 3.2 | 1.0 | 1.0 |

Scale: 5-0%, 4-25%, 3-50%, 2-75%, 1-100% (Percentage of leaf area discolored)
a - Indicates insufficient data.

Control samples were of a crisp texture and medium to dark green color, with few to no blemishes or tears in the leaf prior to treatment. All of the samples were initially judged to have a rating of 5. After drying samples for 1 h in the biosafety hood, leaves were somewhat less crisp due to moisture loss; however, the color did not degrade during drying. Treated samples showed increased wilting and discoloration after storage. Discoloration and wilting increased with longer storage times. Samples treated with air ANEP changed from the initial solid green color to having spots of yellowish-brown discoloration after 0.5 h of storage. Samples treated with oxygen ANEP changed from solid green to having solid white spots after 0.5 h of storage. Discoloration usually occurred at the stem and outer edges of the leaf. Leaves treated with oxygen ANEP seemed to maintain their original green color most effectively in the unaffected portions of the leaves. Leaves treated with air ANEP tended to degrade in color over the entire area of the leaf. Occasionally, samples stored for 0.5 hr showed no discoloration; however, all samples recovered after 0.5 h of storage had high levels of E. coli O157:H7 still surviving on the leaf. Refrigerated samples tended to show a greater crispness than samples stored at room temperature. This observation suggests that spinach leaves should be placed in a refrigerated environment as soon as possible after harvest in order to lessen quality degradation when treated with ANEP. Tests are still underway to assess physical quality changes in the leaves. Particularly, tests need to be conducted to determine the color change of untreated leaves after similar storage periods.

The treatment method utilized in this study of spinach was a scenario in which maximum concentrations of ozone and nitrous oxides could be produced without causing further heating of electrodes. While this method shows effective reductions of spoilage organisms and pathogens, changes in the protocol may need to be made in order to maintain quality of leaves, or any other produce, while still reducing microorganisms to safe levels.

The results of this experimental study suggest that an ANEP treatment system may be capable of reducing spoilage organisms and pathogens, such as E. coli O157:H7, on prepackaged, ready-to-eat spinach leaves. This means that spinach leaves, or nearly any produce, can be packaged prior to treatment, avoiding the possibility of cross-contamination. The packaged produce could be treated with ANEP at the packaging facility and then shipped to market. During shipment, spoilage organisms would be reduced and pathogens would be eliminated, with no residual chemicals or gases. Products would arrive at the grocery store safer and fresher.

In contrast to free-air or moving air techniques, a substantial fraction of the reactive species produced in the ANEP may be caused to be formed and retained within the sample container. Apart from being an efficient use of the power devoted to ionization, the reactive species formed within the container remain within the container until they become neutralized by natural chemical processes. As such, the reactive species created may be expected to remain in proximity to the object to be treated for a longer period of time than when the object has not been packaged. Personnel are not exposed to the ANEP products directly.

Informal experiments were performed using lettuce, tomato, apple, both whole and sliced, cranberries, bologna slices, skin, eggs, both individually and in a carton, plant seeds, and a glass pill bottle, with pills inside. All of the test samples were placed in a plastic bag of suitable size, similarly to the approach used with the spinach samples. The glass pill bottle was also treated as the container itself.

Generally there were two configurations of packaging used. For the individual eggs and the apple, as an example, the storage bag was placed in the DBD apparatus such that the sample was disposed between the electrode plates as shown in FIG. 2A. In other examples, the sample was not disposed between the electrode plates, so that the electrode plates could be brought physically closer together as shown in FIG. 2B. The treatment with the sample "in-field" may expose the sample to direct, short term, ionization products, whereas treatment with the sample "out-of-field" may limit the exposure to longer lifetime ionization products.

For purposes of visualization of the ANEP created, a helium (He) fill was used in some experiments, as the voltage gradient needed for He ionization is about one tenth of that needed for air or oxygen as working gasses. As the particular experimental apparatus was limited to about 18 kV and 60 Hz, the He MAP permitted visualization of effects which were likely to be obtained in air or $O_2$ mixtures using higher voltages and greater electrode spacings than in the spinach experiments described previously, and where in-field exposure would occur.

The ionization characteristics of other noble gases such as Ar and Xe is similar to He at near atmospheric pressure. While the visualization MAP was a relatively pure noble gas, observations of gas mixtures comprising a smaller amount of noble gas and other gases such as $O_2$, $N_2$, $CO_2$ and $H_2O$ exhibited similarly lowered ionization energy requirements. This may arise from the noble gas forming a glow discharge and providing seed paths for the ionization of some or all of the remaining constituent gases. So, either the applied voltage may be decreased, or the DBD gap increased. That is, the product of the applied voltage and the gap distance needed to create an ANEP would be reduced with respect to a MAP that did not use a noble gas as a constituent. Observations of an ANEP with He as the MAP were made at 18 KV and a gap of 10 cm; a similar effect may be expected with a MAP where He is a constituent. This means that the object to be treated may be placed directly between the electrode plate and the dielectric barrier, even in the case of a head of lettuce.

A brief series of experiments was conducted to evaluate the required voltage gradient for a working gas having a noble gas as a component gas. The same experimental arrangement as for the egg example was used, except that there was no object to be treated within the container.

The minimum voltage gradients needed for the creation of an ANEP, based on working gas composition, were determined to be:

100% He—4.5 kV/in;
50% He/50% air—16.8 kV/in;
10% He/90% air—24 kV/in; and
100% air—43.2 kV/in.

Since the voltage gradient needed to create an ANEP in a working gas having a noble gas component is less than the voltage gradient needed in air, the ANEP may be created in the storage volume without the likelihood of a plasma discharge occurring in the region surrounding the storage volume. That is, a direct discharge between the plates of the DBD apparatus would require a higher voltage than is needed to create the ANEP within the storage volume. In addition to increasing the distance between the plates that can be used for a fixed apparatus voltage, a noble gas component of the working gas would permit the entire storage area to be located between the plates of the DBD apparatus and the ANEP created inside the entire storage volume not occupied by the object without creating ozone in the free air space surrounding the package.

Providing that the available voltage is sufficient to produce an ANEP plasma within the package, only a small percentage of the working gas need be a noble gas such as He, Ar, or Xe, to reduce the ionization voltage gradient within the package to less than that of the surrounding air. Since a 10% He component of the working gas reduced the ionization gradient by almost a factor of two, perhaps 5% or less may reduce the relative ionization potential within the package with respect to the surrounding environment so as to permit the ANEP generation to be confined within the package, yet permit the entire package to be subject to the dielectric-barrier-discharge effect. The specific percentage of noble gas in the working gas mixture will depend on the apparatus geometry, the effects of the objects in the storage volume, and the other constituent gases. However, the specific values can be determined by experimental studies.

Where the breakdown voltage gradients in the storage volume and in the surrounding air are essentially the same, the electrode area of the DBD is generally selected so as not to be large enough to produce an ANEP in the entire storage volume, as there is the risk that a more substantial discharge would occur in the air environment. Such discharges result in reactive species generation, to which personnel would be exposed, and may also result in pinholes in the storage volume surface.

Where food is the object to be treated, the object may be considered as a dielectric. Although the dielectric may be imperfect, the losses are likely to be small at low frequencies. The voltage distribution between the electrodes of the DBD will be modified by the presence of the object so that the effective voltage gradient in the working gas gap between the dielectric of the DBD apparatus and the object is increased. This may further decrease the voltage that may need to be applied in order to initiate ANEP plasma.

In another aspect, it seems likely that the working voltage may be decreased after the ANEP plasma has been initiated. The selection of gas mixtures may depend on the product and packaging characteristics as each type of product may have an optimal MAP, treatment time, storage conditions, or the like. A person of skill in the art would understand that a series of optimization experiments would be conducted to obtain the optimum parameters in each case.

Figure 3:
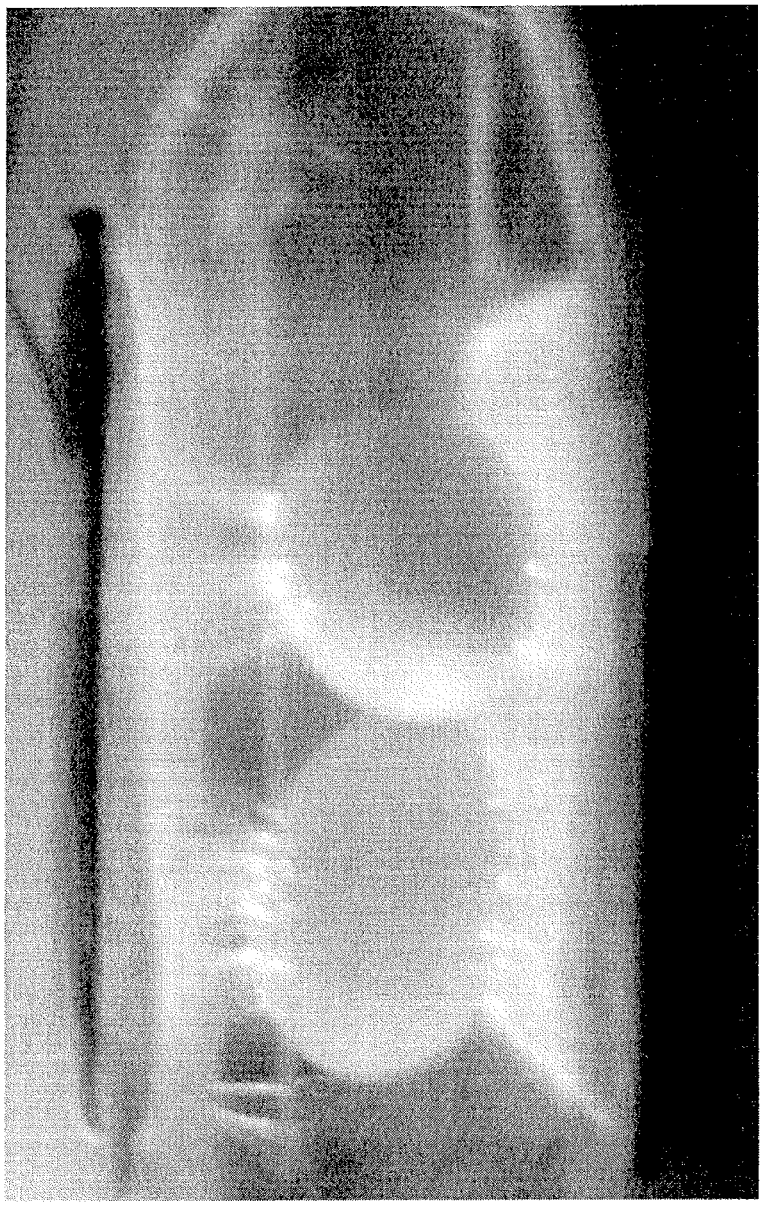
FIG. 3 is a photograph of two eggs disposed in a DBD apparatus with a He MAP atmosphere where an ANEP plasma is active; filamentary discharges are seen terminating on the surface of the eggs.

FIG. 3 shows an example of two eggs, enclosed in a plastic bag subject to in-field ANEP exposure with He as the MAP working gas. The filamentary nature of the DBD discharge is clearly seen, with the streamers terminating on the eggs and on the package. A more diffuse discharge is present in the region between the DBD electrodes where there is no egg. The specific arrangement of streamers would depend on the surface characteristics of the object as a dielectric, such as roughness, contaminants and the like, and that of the container, and may differ for different products to be treated. The streamers appear to be preferentially formed between the DBD electrodes and DBD dielectric and the egg, where the egg acts as a dielectric object disposed between the plates. This result appears qualitatively consistent with the voltage gradients that would obtain in the region without an ANEP present.

An apple was also treated in a He MAP atmosphere, similarly to the egg sample shown in FIG. 3, so as to visualize the process. The apple was located between the plates of the DBD apparatus, and ionization of the He MAP was possible at the 15 KV potential due to the lower ionization voltage required. After exposure, the apple was removed from the bag and distinctly smelled of ozone. This may arise from the property of apples that about 20 percent of the volume thereof is formed by small air sacs. The ozone may be produced by ionization of the air in the sacs. Alternatively, the skin may be the region in which the ozone formation occurs. In either case, the formation of the ozone may lead to improvements in at least the surface cleanliness and storage life. Other fruits and vegetables may also benefit from this treatment. Treatment of sliced or diced product should also be practical. The use of He in the experiment and the absence of $O_2$ in the gas mixture enabled the smell detection of the ozone produced within the apple or remaining on the surface thereof.

While the present experiments have focused on food products, the same techniques may be used for medical equipment or other objects to be rendered less contaminated or sterile within a package. Based on the observations of the ionization characteristics produced in the reported experiments, it was possible to recognize that placing plastic tubing between the electrodes, with the electrodes close to or contacting the tube, may result in forming an ANEP plasma within the tube, thus processing the interior portion of the tube. The exterior of the tube, enclosed in the overall packaging, may be processed by using the same or a greater electrode spacing so that an ANEP may be formed within a package containing the tubing. Alternatively, there should be a voltage gradient range where both processes may occur with a single electrode spacing. Other gas mixtures may be used in medical equipment processing, which may not be considered appropriate for consumable products. A variety of medical devices, including metallic devices may be similarly treated.

In the previous examples, the bag was closed, and remained closed during the treatment and the storage. However, depending on the objective of the treatment, and the desired after storage conditions, the bag may be punctured, opened, perforated, or the like. Depending on the specific apparatus configuration, the bag may be partially ventilated with holes. This may permit the generation of an ANEP plasma jet in the bag or package, similar to that being developed as thrusters in avionics.

Figure 4A:
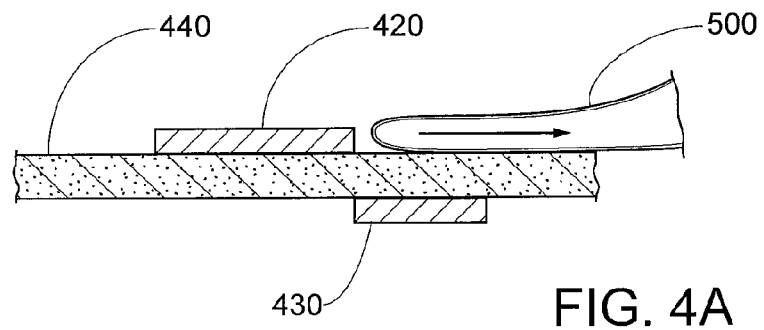
FIG. 4 shows an example of portion of a DBD apparatus where a plasma jet or asymmetrical ANEP can be created in (A) a side view; and, (B) a top view; and, (C) an end cross section view of a portion of cardboard box having the DBD apparatus electrodes configured to be placed along an outer edge thereof.
Figure 4B:
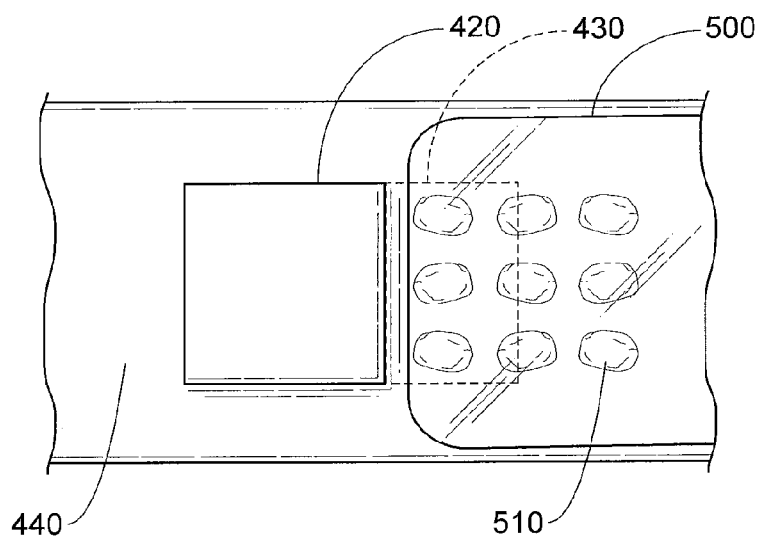

FIGS. 4 A and B illustrate a configuration where a bag 500 containing an object to be treated 200 has apertures and the DBD has at least one electrode 420 that is not dielectric coated or isolated. The dielectric 440 is disposed between the exposed electrode 420 and the lower electrode 430 so that an ANEP is formed in the region of the surface of the dielectric 440 and terminating at the exposed electrode 420. In such an example, the processes at the instantaneous anode and the cathode electrodes may not be the same, and a person of skill in the art would expect a plasma jet to be generated. Even when the bag does not have apertures 510, the asymmetrical nature of the ANEP generation may lead to gas currents. The gas currents associated with such a jet or asymmetrical ANEP generation, produced internal to the bag, could be effective in distributing the reaction products throughout the bag, and mitigating a heat rise in the bag so that a more intense discharge may be used.

Figure 4C:
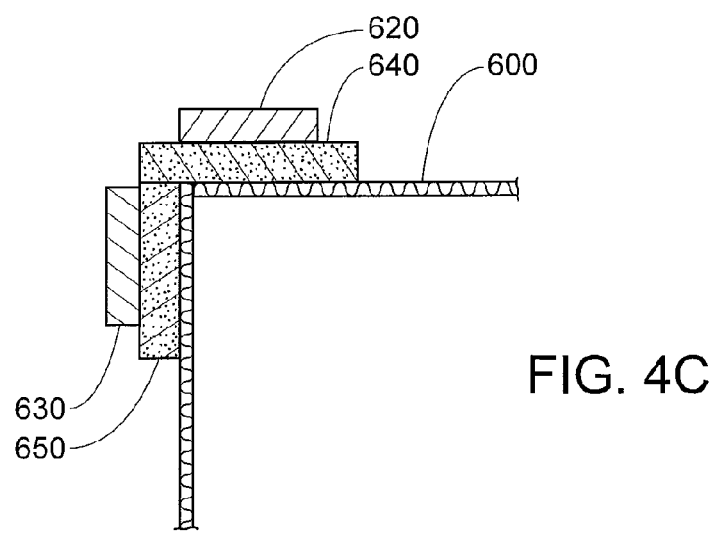

FIG. 4C illustrates a situation where the DBD apparatus may be used to process objects that have been stored in a substantially dielectric container, such as a cardboard box. The interior of the box may be sealed with a plastic layer or a foil layer, although this is not needed in all applications. The electrodes 620 and 630 are protected from excessive discharge current by the dielectric layers 640 and 650, and the electrodes are disposed at an approximately right angle to each other, and placed along the edge of the container so that the ANEP is formed in the interior angle therebetween.

The term bag has been used to represent the enclosure, container, treatment volume or storage volume in which the object is treated and subsequently stored. However, this should be understood to represent any dielectric material compatible with the treatment process, and could be a bottle, a vial, an opaque plastic food tray sealed with a thin transparent film, or the like. The objects to be processed need not be dielectric, as metallic objects could be exposed as well. The metal surfaces would likely behave similarly to the metal surface that is not covered with a dielectric in case where only one of the electrodes is dielectric protected. Thus, the apparatus and technique may be used to sterilize or otherwise decontaminate objects such as medical supplies, including surgical instruments, syringes, and the like so that they do not need to be removed from the packaging after treatment and until immediately prior to use. One may repeat the sterilization process in the hospital or physician's office prior to opening the packaging for further suppressing contaminants or pathogens. It should be noted that the dielectric forming the container may be used as the dielectric barrier of the DBD, providing that the electrical characteristics thereof prevent dielectric breakdown.

Figure 5:
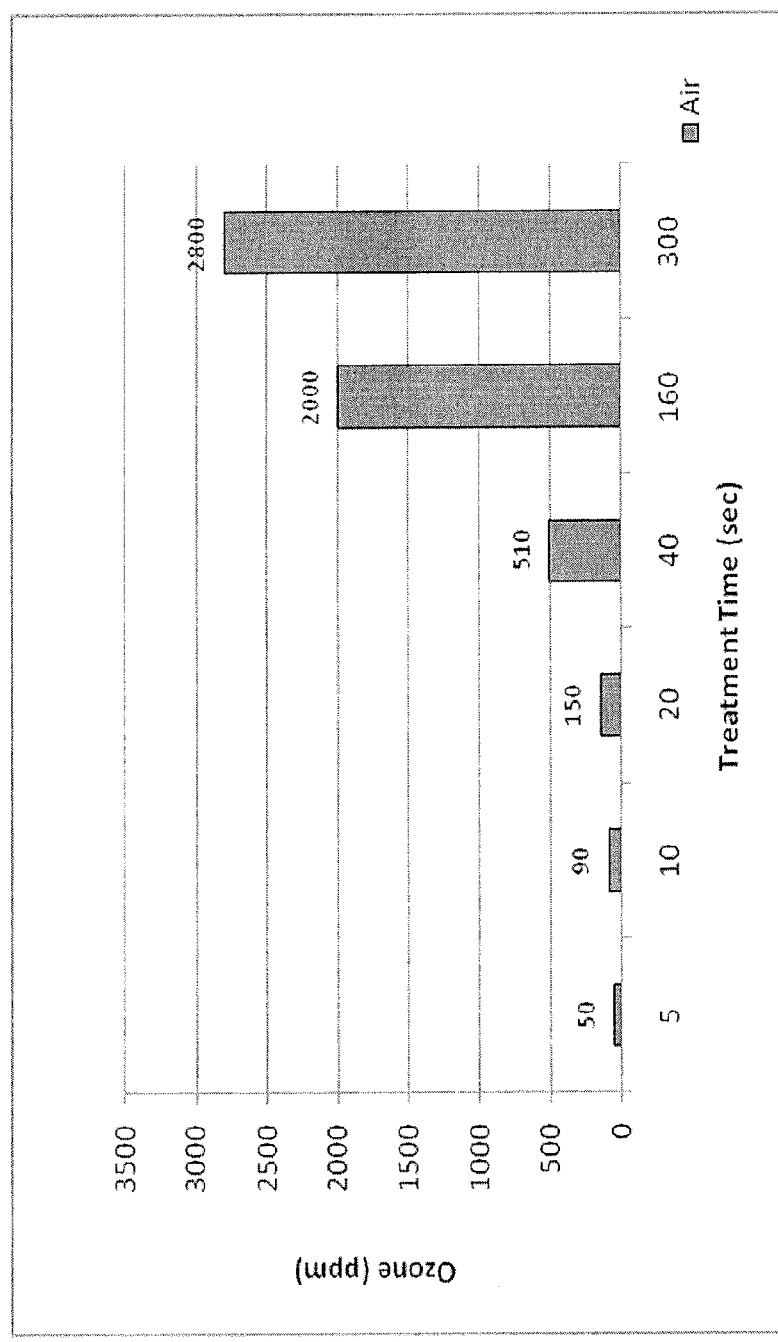
FIG. 5 shows the concentration of ozone in the package as a function of the time duration of the ANEP generation for a MAP having the characteristics of air.

As may be expected, the ozone concentration increases with the time duration of ANEP generation, being dependent, for each reactive species, on the details of the recombination process. FIG. 5 shows the results of tests where the ozone concentration was measured as a function of the duration of ANEP generation. Preliminary tests at higher voltages suggest that an increase in the rate of reactive species generation may be possible, and that the electrode gap may also be increased.

Thus, objectives of the treatment of an object using in-storage-volume ANEP generation may vary depending on the particular circumstance, ranging from improving the storage characteristics by reducing surface contamination, reducing the number of colony forming units (CFU) of bacteria related to spoilage or species that are human pathogens, sterilization of the food or object, or the like. Each circumstance will determine the gas composition, plasma concentration and exposure time that may be appropriate.

Although only a few exemplary embodiments have been described in detail above, those skilled in the art will readily appreciate that many modifications are possible in the exemplary embodiments without materially departing from the novel teachings and advantages of the invention. Accordingly, all such modifications are intended to be included within the scope of this invention as defined in the following claims.

The invention claimed is:
1. A method of decontaminating an object, comprising:
   providing a dielectric barrier discharge (DBD) device;
   providing a container suitable for completely enclosing the object and a working gas;

inserting the object and the working gas into the container and closing the container prior to activating the DBD device;

disposing a portion of the closed container with respect to the DBD device such that reactive species are produced in the closed container; and activating the DBD device for a first period of time, wherein the DBD device comprises a pair of electrodes, spaced apart and disposed outside the container, with a dielectric material disposed between at least one of the pair of electrodes and the portion of the closed container in which an atmospheric non-equilibrium plasma (ANEP) is to be created by the DBD device; and, the closed container is not completely enclosed by another structure when the DBD device is activated.

2. The method of claim 1, wherein the working gas comprises a noble gas selected from one more of He, Ar, or Xe.

3. The method of claim 2, wherein a percentage of the noble gas is greater than about 5 percent by volume of the working gas.

4. The method of claim 2, wherein a percentage of noble gas is greater than about 10 percent by volume of the working gas.

5. The method of claim 1, wherein the ANEP is comprised of reactive species formed from the working gas.

6. The method of claim 5, wherein the reactive species comprise free radicals.

7. The method of claim 5, wherein the reactive species comprise at least two of: ozone, NO, $NO_2$, $N_2O$, $N^+$, $O^+$, $OH^+$ or $H_2O_2$.

8. The method of claim 1, wherein the ANEP is formed as a plasma jet.

9. The method of claim 1, wherein the ANEP is created by electrodes oriented at an angle of less than or equal to 90° to each other.

10. The method of claim 1, wherein the container is a sealable dielectric bag.

11. The method of claim 1, wherein the container has sealable opening adapted to receive the object when the opening is in an open configuration.

12. The method of claim 1, wherein the container is made of a substantially dielectric material.

13. The method of claim 12, wherein the container is made at least in part of a plastic or a glass.

14. The method of claim 12, wherein the container is a sealable plastic bag.

15. The method of claim 1, further comprising:
retaining the object within the container for a second period of time commencing after completion of the first period of time.

16. The method of claim 15, further comprising:
deactivating the DBD device after completion of the first period of time.

17. The method of claim 16, wherein a sum of the first period of time and the second period of time is selected to result in decontamination of the object.

18. The method of claim 17, further comprising:
retaining the object within the container after completion of the second period of time.

19. The method of claim 15, wherein a sum of the first period of time and the second period of time is selected to result in sterilization of the object.

20. The method of claim 15, wherein the second period of time is selected so that reaction products of the ANEP have decayed to a predetermined level.

21. The method of claim 1, further comprising:
filling the container with a predetermined working gas mixture.

22. The method of claim 21, wherein the container is a re-sealable container.

23. The method of claim 22, wherein the container is sealed after introduction of the object and the working gas.

24. The method of claim 1, wherein the working gas includes a noble gas in a quantity sufficient to reduce a voltage needed for the DBD device to produce an atmospheric non-equilibrium plasma (ANEP) in the container to a value below a voltage need to produce a ANEP in an ambient environment.

25. The method of claim 1, wherein the working gas includes a noble gas in a quantity sufficient to reduce a voltage needed for the DBD device to produce an atmospheric non-equilibrium plasma (ANEP) in the container with respect to a voltage needed to create the ANEP for a working gas not including the noble gas, by about at least 10 percent, for a fixed apparatus geometry.

26. The method of claim 1, further comprising:
providing a power supply, connected to the pair of electrodes, having a voltage of at least about 65 kV (root-mean-square) and less than about 120 kV (root-mean square).

27. The method of claim 1, wherein the object is not disposed between the pair of electrodes.

28. The method of claim 1, wherein planar dimensions of the electrodes are less than corresponding planar dimensions of the container.

29. A method of treating an object, comprising:
packaging the object to be treated in a closed container, a volume of the container not containing the object being filled with a working gas at substantially atmospheric pressure;

placing the packaged object in an apparatus for generating an atmospheric non-equilibrium plasma (ANEP) in the closed container, which is otherwise not completely enclosed;

activating the apparatus for a time period so as to generate the ANEP inside at least a portion of the container, without producing or emitting the ANEP outside the closed container; and removing the container from the apparatus.

30. The method of claim 29, further comprising:
storing the treated object in the container for a storage period.

31. The method of claim 30, wherein the storage period is one of a shelf life or a time to when the object is be used.

32. The method of claim 30, wherein the time period is selected so as to decontaminate the object after the storage period.

33. The method of claim 30, wherein the time period is selected so as to sterilize the object after the storage period.

34. The method of claim 30, wherein the object remains in the container after the storage period.

35. The method of claim 29, wherein a storage period is substantially greater than the time period where the ANEP is generated.

36. The method of claim 29, wherein the working gas comprises one or more gases selected from: air, oxygen, nitrogen, carbon dioxide, water vapor, or chlorine.

37. The method of claim 29, wherein the working gas is a modified atmosphere packaging (MAP) mixture.

38. The method of claim 28, wherein the working gas includes a noble gas.

39. The method of claim 38, wherein the working gas includes a noble gas in a quantity sufficient to reduce a voltage required to create the ANEP in the container with respect to a voltage needed to create the ANEP for a working gas not including the noble gas, by about at least 10 percent, for a fixed apparatus geometry.

40. The method of claim 29, wherein the working gas comprises air.

41. The method of claim 29, wherein the working gas comprises oxygen.

42. The method of claim 29, wherein the working gas comprises oxygen and nitrogen.

43. The method of claim 29, wherein the working gas comprises less than or equal to about 10% $CO_2$ by volume.

44. The method of claim 43, wherein the working gas further comprises H20.

45. The method of claim 29, wherein the working gas comprises at least 5% % $N_2$ by volume.

46. The method of claim 29, wherein the container has a sealable opening adapted to receive the object when the opening is in an open configuration.

47. The method of claim 29, wherein the apparatus for generating the ANEP is a dielectric barrier discharge (DBD) device.

48. The method of claim 29, wherein the container has an aperture disposable such that one of two electrodes of a DBD apparatus is facing the aperture.

49. The method of claim 48, wherein the DBD apparatus further comprises a solid dielectric material disposed between at least one of a first electrode or a second electrode and the container.

50. The method of claim 29, wherein the container is made of a substantially dielectric material.

51. The method of claim 29, wherein the container is made at least in part of a plastic or a glass.

52. The method of claim 29, wherein the volume container is a sealable plastic bag.

53. The method of claim 29, wherein an operation voltage of at least about 65 kV (root-mean-square) and less than about 120 kV (root-mean square) is applied to pair of electrodes of the apparatus to produce the ANEP.

54. A method of treating an object, comprising:
providing a dielectric barrier discharge (DBD) device;
placing the object to be treated in a container;
introducing a working gas to the closed container at substantially atmospheric pressure and closing the container;
disposing at least a portion of the container with respect to the DBD device such that reactive species are produced only in the object or the working gas in the closed container when the DBD is activated; and
activating the DBD,
wherein a geometry of the DBD device, the working gas and an operation voltage are selected so as to preclude production of reactive species outside of the closed container when an electrode of the DBD device is not completely enclosed by another structure.

55. The method of claim 54, wherein a dielectric is disposed between the electrode and the closed container.

56. The method of claim 55, wherein the electrode is surrounded by the dielectric.

57. The method of claim 54, further comprising:
providing a power supply, with an operation voltage of at least about 65 kV (root-mean-square) and less than about 120 kV (root-mean square).

* * * * *

UNITED STATES PATENT AND TRADEMARK OFFICE
CERTIFICATE OF CORRECTION

PATENT NO. : 9,539,352 B2  
APPLICATION NO. : 13/793342  
DATED : January 10, 2017  
INVENTOR(S) : Kevin M. Keener et al.

It is certified that error appears in the above-identified patent and that said Letters Patent is hereby corrected as shown below:

In the Claims

In Column 20, Claim 38, Line 66, after "The method of claim" replace "28," with --29,--.

In Column 22, Claim 52, Line 3, after "claim 29, wherein the" delete "volume".

Signed and Sealed this  
Nineteenth Day of December, 2017

Joseph Matal  
*Performing the Functions and Duties of the*  
*Under Secretary of Commerce for Intellectual Property and*  
*Director of the United States Patent and Trademark Office*